United States Patent [19]
Haas

[11] 4,221,206
[45] Sep. 9, 1980

[54] CARBON MONOXIDE DETECTOR AND DEACTIVATING MECHANISM

[76] Inventor: Robert G. Haas, 1019 Grandview, Lockport, Ill. 60441

[21] Appl. No.: 960,331

[22] Filed: Nov. 13, 1978

[51] Int. Cl.² .................... F02D 11/04; F02D 11/10; G01N 27/16
[52] U.S. Cl. .............................. 123/198 DC; 422/83; 422/93; 422/96; 422/98; 73/23
[58] Field of Search ...................... 422/83, 93, 94–98; 73/23; 123/198 D, 198 DC; 180/82 R

[56] References Cited
U.S. PATENT DOCUMENTS

| | | | |
|---|---|---|---|
| 2,857,251 | 10/1958 | Krogh | 422/94 |
| 2,879,663 | 3/1959 | Thomas | 422/96 X |
| 2,883,270 | 4/1959 | Johnson | 422/96 |
| 2,916,358 | 12/1959 | Valentine et al. | 422/96 |
| 2,949,765 | 8/1960 | Thayer | 422/96 X |
| 3,399,398 | 8/1968 | Becker et al. | 422/98 X |
| 3,440,017 | 4/1969 | Palmer | 422/95 |

OTHER PUBLICATIONS
M.S.A. CO Alarm Catalog No. 4, Bulletin DR-1.

Primary Examiner—Michael S. Marcus
Attorney, Agent, or Firm—Ernest Kettelson

[57] ABSTRACT

A carbon monoxide detector and deactivating mechanism to monitor the level of carbon monoxide concentration within the passenger compartment of a vehicle having an internal combustion engine, and to stop the operation of such internal combustion engine when the level of carbon monoxide concentration reaches a danger point for occupants of the passenger compartment. The detector includes plural detecting means to determine such dangerous concentration level, at least two of which detect carbon monoxide in the atmosphere by different methods and principles of operation. The detector is electrically connected to the vehicle's electrical system and when the critical pre-determined level of carbon monoxide is reached, it triggers a vacuum switch to interrupt the ignition circuit of the vehicle for a long enough time to insure that the internal combustion engine has been stopped.

4 Claims, 6 Drawing Figures

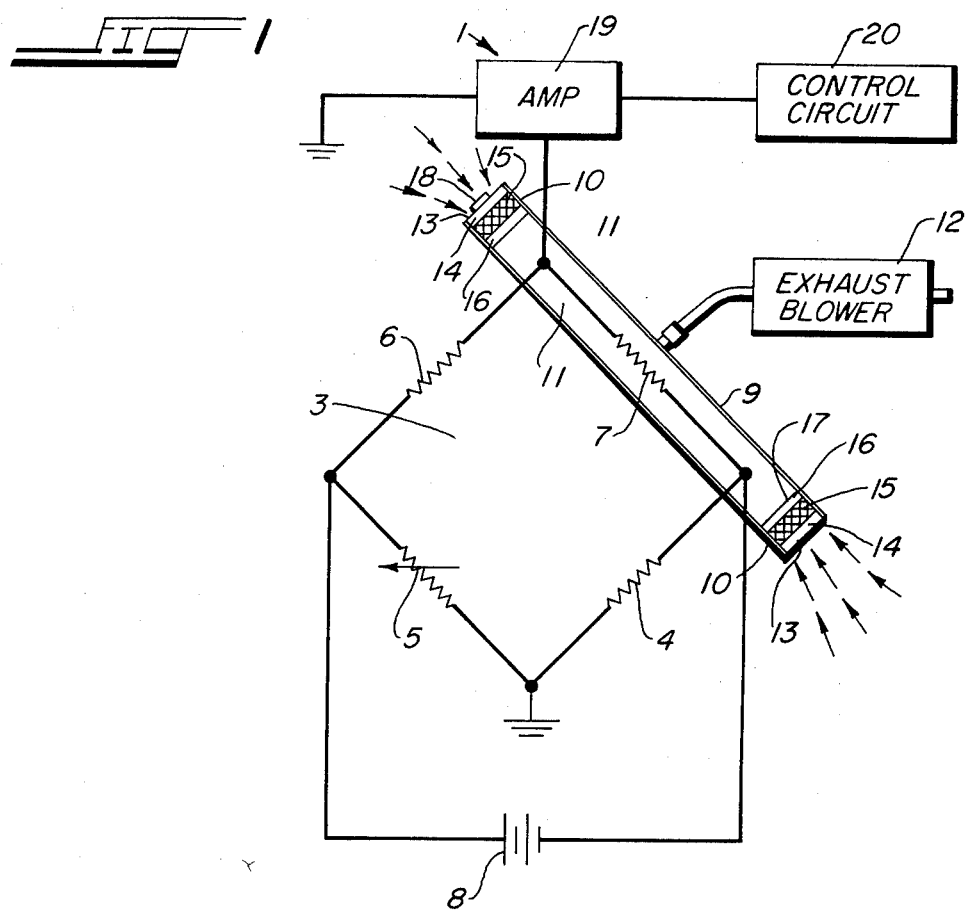
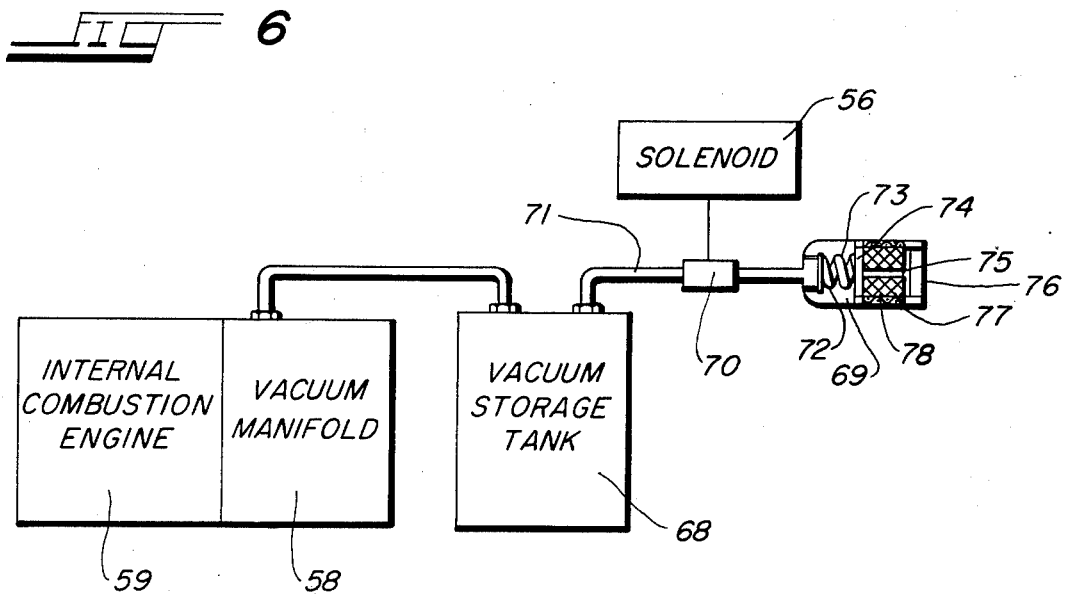

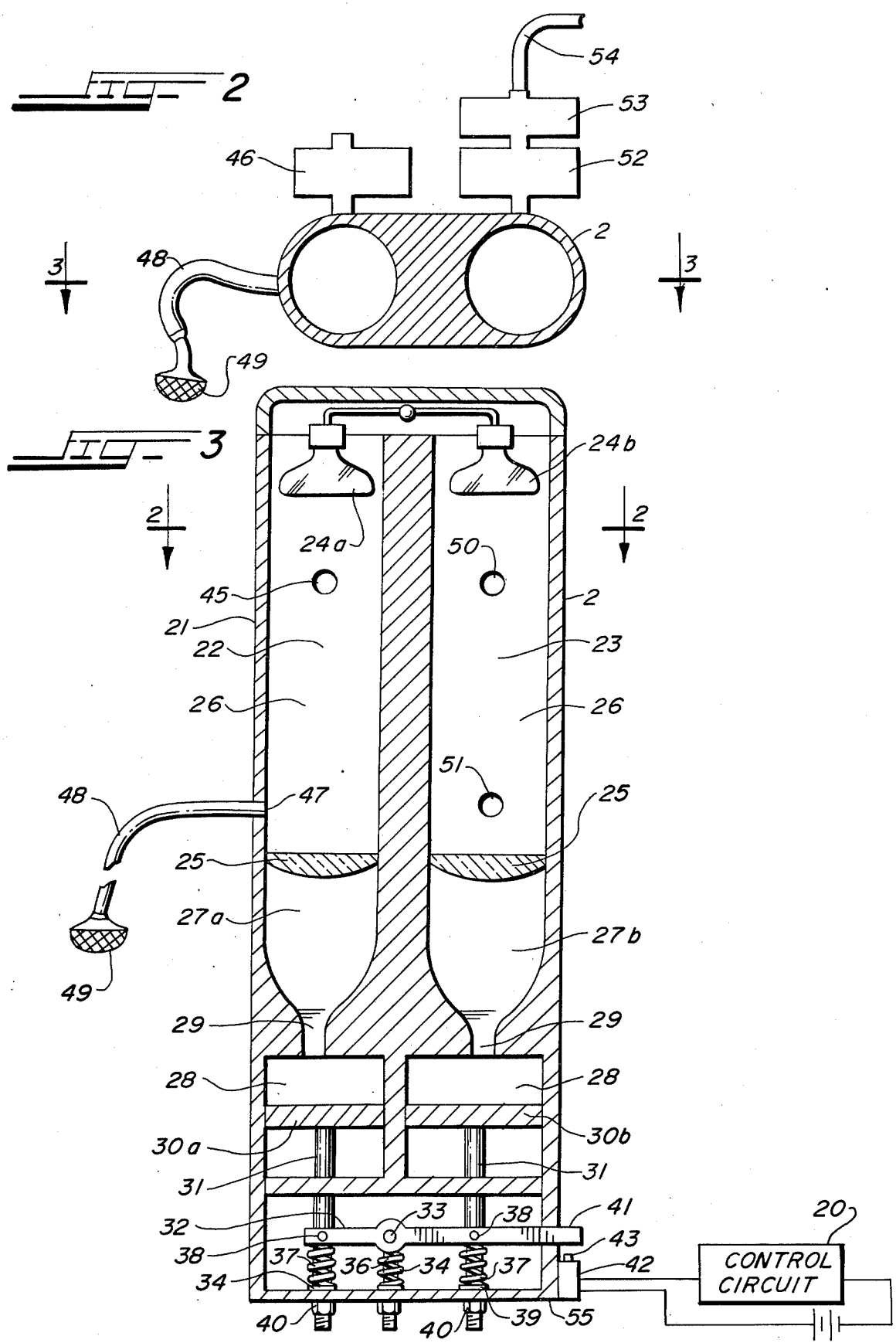

CARBON MONOXIDE DETECTOR AND DEACTIVATING MECHANISM

BACKGROUND OF THE INVENTION

This invention relates to the field of carbon monoxide detectors and control mechanisms associated therewith.

Apparatus and methods to detect the presence of carbon monoxide in the atmosphere have been developed and are known to the prior art. However, since carbon monoxide is odorless, colorless and tasteless it is a difficult gas to detect, to differentiate from other gases, and to measure its relative concentration in a given volume of air. Some of the known methods of detecting and measuring the amount of carbon monoxide in air, actually measure the amount of some other gas such as carbon dioxide which is more easily detected and measured. Then the ratio of carbon monoxide to carbon dioxide is calculated for given conditions, which gives a rough approximation and is a suitable detector of carbon monoxide for various purposes. However, for use in stopping the engine of a vehicle when a critical danger level is reached, the detecting mechanism must be relatively precise or the engine may cut out while underway and at a dangerous point, such as when passing another vehicle in the face of oncoming traffic in the passing lane, even though the carbon monoxide level within the passenger compartment had not reached the critical point of becoming a danger to the driver and passengers. Another known method of detecting and measuring the concentration of carbon monoxide in air is by measuring the change in electrical current passing through a silver oxide pellet when carbon monoxide is present. However, this relatively recent discovery as disclosed in U.S. Pat. No. 3,970,431 which issued July 20, 1976, is limited in its application, since the reaction of carbon monoxide with the silver oxide medium is irreversible at higher concentrations, such as above 30 parts per million. Thus, if the concentration of carbon monoxide is above 30 parts per million, the silver oxide pellet or other medium cannot be used again. For the purpose of the present invention, such a prior art method of carbon monoxide detection and measurement would be impractical, not to mention expensive. The level of carbon monoxide concentration in air which approaches the danger level for humans is about 0.14% at the low end and a 0.4% level maintained for about 30 minutes is nearly always fatal. Thus, a detector for the purpose used in the present invention must be operable at some point between 140 and 400 parts per million of carbon monoxide in the atmosphere. Also, a silver oxide pellet or other medium would have to be rigorously protected and shielded from the atmosphere until ready for use. Otherwiseit may be inadvertently exposed to an atmosphere in which a relatively small amount of carbon monoxide is present, e.g. above 30 ppm but below 140 ppm, in which case the silver oxide would become contaminated and irreversibly reacted with the carbon monoxide in the air.

Another method of detecting carbon monoxide known to the prior art is the use of a Wheatstone bridge, comprising balanced resistors in a bridge circuit, one of which is utilized as a sensor to detect the presence of carbon monoxide. The resistor which functions as a sensor is enclosed within a chamber into which continuous samples of the atmosphere are admitted for contact with the resistor. The sensing resistor may be combined with a material such as hopcalite which has properties capable of distinguishing carbon monoxide from hydrogen and other gases which may be present in the atmosphere. Hopcalite is a catalyst which was developed some sixty years ago, about 1918, and which oxidizes carbon monoxide in any air which contacts and passes through the hopcalite material. Thus, when air containing a concentration of carbon monoxide enters the sensing assembly comprising a combination of the sensing resistor and hopcalite, it will oxidize thus raising the temperature of the sensing resistor causing a change in current flow through such resistor. Current flow will increase or decrease depending on whether the resistance material has a positive or negative temperature coefficient of resistance. In either event, the Wheatstone bridge will become unbalanced thus indicating the presence of carbon monoxide. An example of this type of detector is disclosed in U.S. Pat. No. 2,879,663 which issued Mar. 31, 1959.

One problem with the Wheatstone bridge type of detector is its reliability, and its ability to distinguish between carbon monoxide and hydrogen or other gases. Under certain circumstances or conditions, the sensing resistor assembly may oxidize or cause combustion in the presence of gases other than carbon monoxide, or other than a pre-determined level of carbon monoxide concentration which could have catastrophic effects if continued operation of the internal combustion engine of a vehicle were being controlled by such a detecting mechanism.

It is for that reason among others that the present invention includes the use of a plurality of carbon monoxide detectors, at least two of which operate on differing principles so one is a type of "fail-safe" check on the other and both must indicate the pre-determined level of carbon monoxide concentration in the atmosphere within the passenger compartment of the vehicle before initiating the control mechanism which will stop operation of the internal combustion engine, the source of the carbon monoxide gas.

SUMMARY OF THE INVENTION

It is an object of the invention to provide a detecting mechanism for detection of a pre-determined level of carbon monoxide concentration in the atmosphere within the passenger compartment of a vehicle powered by an internal combustion engine.

It is an object of the invention to provide a detecting mechanism for detection of a pre-determined level of carbon monoxide concentration in the atmosphere within any chamber, compartment or room which may be fed by fumes from an internal combustion engine.

It is an object of the invention to provide a detecting mechanism for detection of a level of carbon monoxide concentration in the atmosphere of a compartment or chamber above approximately 0.14% or 140 parts per million and before it reaches approximately 0.4% or 400 parts per million.

It is an object of the invention to provide a detecting mechanism for detection of a dangerous level of carbon monoxide concentration within the passenger compartment of a vehicle powered by an internal combustion engine and a deactivating mechanism which will stop the operation of such internal combustion engine on occurence of such dangerous level of carbon monoxide concentration but not before.

It is an object of the invention to provide a detecting mechanism for detection of a pre-determined level of carbon monoxide concentration which includes a plurality of detectors at least two of which operate on different principles to detect the presence of carbon monoxide.

BRIEF DESCRIPTION OF THE DRAWING

FIG. 1 is a partially schematic view of an electrical detector of carbon monoxide in accordance with this invention.

FIG. 2 is a sectional view taken on line 2—2 of FIG. 3 showing a mechanical detector of carbon monoxide in accordance with this invention looking down from the top.

FIG. 3 is a sectional view taken on line 3—3 of FIG. 2 showing a section of the mechanical detector of FIG. 2 in elevation.

FIG. 6 is a partially block diagram view of an auxiliary vacuum supply source and a fresh air vent operated thereby.

DESCRIPTION OF PREFERRED EMBODIMENT

Figure 4:
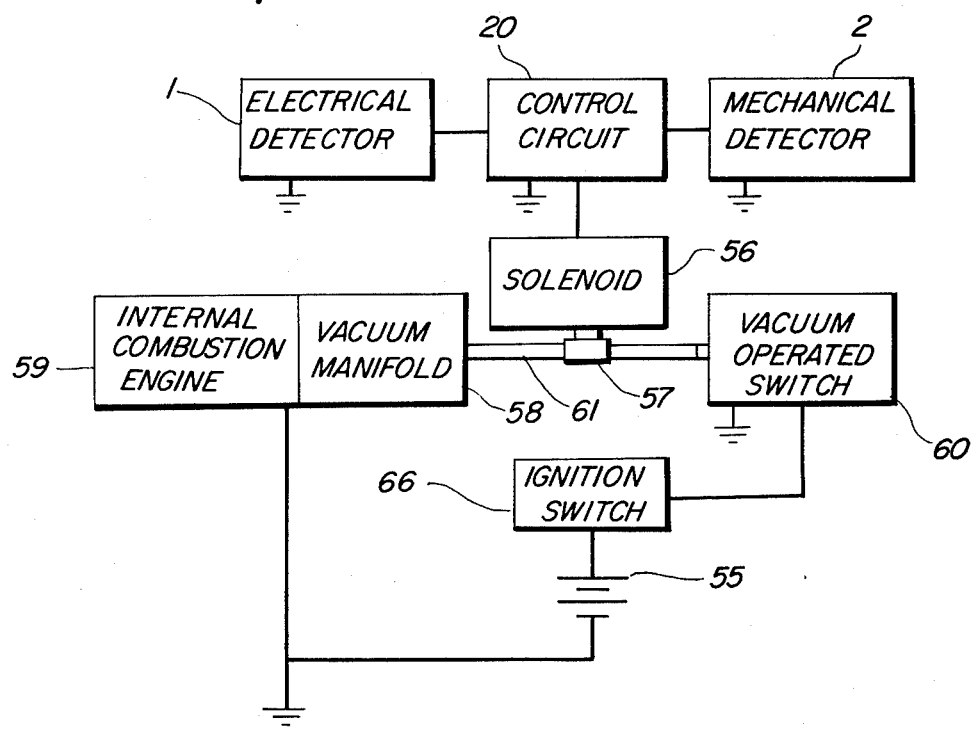
FIG. 4 is a block diagram view of the carbon monoxide detection system in accordance with this invention.
Figure 5:
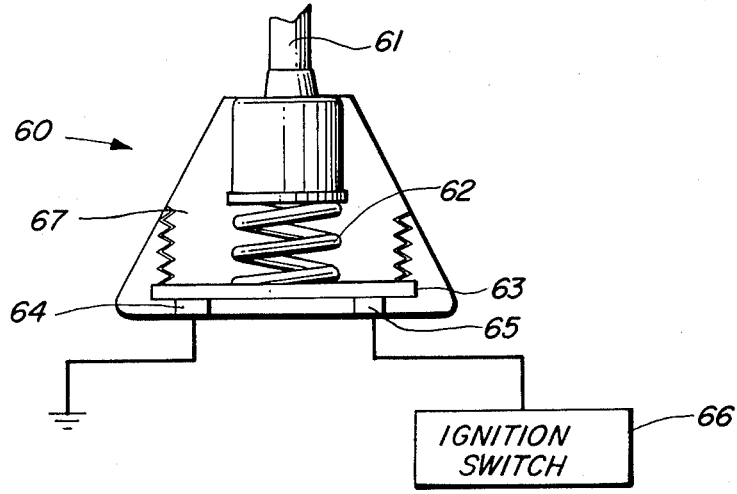
FIG. 5 is a section view of the vacuum operated switch in accordance with this invention.

The mechanism for detecting a preselected amount of carbon monoxide in the air includes an electrical detector 1 and a mechanical detector 2, each operating on a different principle to detect the preselected level of carbon monoxide concentration. Both have to sense the prescribed amount before any action will be initiated to bring the internal combustion engine which is emitting the carbon monoxide to a stop.

The electrical detector 1 includes a balanced impedance circuit or Wheatstone bridge 3, comprising a fixed resistor 4, a variable resistor 5, a balancing fixed resistor 6 and a sensing resistor 7. The sensing resistor 7 is of the type whose resistance varies substantially with temperature. It may for example be a substantially pure iron wire resistor which has a positive temperature coefficient of resistance, so when the temperature of the wire increases its electrical resistance also increases. The bridge is supplied with electrical power from a battery 8. The resistors are chosen to normally be in balance with no output when energized by the battery 8, and variable resistor 5 is adjustable to provide such balance and no output until such time as the sensing resistor 7 detects the presence of carbon monoxide in the surrounding atmosphere.

Resistor 7 detects such presence of carbon monoxide as follows. It is mounted within a tubular housing 9, in each end of which a four part filter 10 is secured through which surrounding air is drawn and filtered into the chamber 11 by operation of the exhaust blower 12. The four part filters 10 which include an outer screen 13 as the first part, a layer of desiccant material 14 such as calcium chloride next as the second part, a layer of hopcalite 15 next inwardly as the third part, and another layer of desiccant material 16 inwardly of and next to the hopcalite layer as the fourth part. An inner screen 17 may be provided inwardly of and adjacent to the inward desiccant layer 16. The filters 10 may be in the form of screw caps, which may be threadedly secured to each end of the tubular housing 9. In this manner, the filters 10 may be replaced when and if necessary to provide fresh hopcalite and desiccant material.

Hopcalite is a catalyst material useful in detecting the presence of carbon monoxide. It is a mixture of metallic oxide, including 50% manganese dioxide, 30% copper oxide, 15% cobaltic oxide and 5% silver oxide, and was developed some sixty years ago in or about 1918. Carbon monoxide is readily oxidized in the presence of this catalyst even at ordinary temperatures and pressures. Hopcalite must be kept dry however, and even moisture in the air can adversely affect its ability to function as a catalyst. It is for that reason that the layers of desiccant material 14 and 16 are provided on both sides of the layer of hopcalite to completely protect it on both sides from any moisture or water vapor.

The tubular housing 9 with sensing resistor 7 therein is mounted within the passenger compartment of the vehicle, or within whatever chamber or compartment is being monitored, with each opposite end exposed to the air in such chamber or compartment. In operation, battery 8 energizes the normally balanced resistance bridge and the exhaust blower 12 draws continuous samples of air from the monitored compartment through the filters 10 into the chamber 11 of tubular housing 9 and across the sensing resistor 7. When air drawn through the filters 10 contains carbon monoxide, the reaction with the layer of hopcalite catalyst material causes a temperature rise. The air flowing across the PTC (positive temperature coefficient) resistor 7 is thus heated, causing a temperature rise in the resistor and a corresponding increase in its resistance. Such increase in resistance unbalances the bridge, causing a voltage output to appear at the outlet terminal 18 leading to amplifier 19. The amplifier 19 in turn provides a signal to control circuit 20, which upon occurrence of a similar signal from the mechanical detector 2 will initiate measures to stop the internal combustion engine which is the source of the carbon monoxide.

The mechanical detector 2 includes a block 21 having two cylinders 22 and 23 formed therein. An infra-red bulb 24 is mounted at one end of each of said cylinders, and a lens 25 is mounted near the opposite end of each cylinder. The lens 25 are sealingly mounted within their respective cylinders to prevent the passage of air or any gas from one side of the lens 25 to the other. Each cylinder is thus divided into two chambers 26 and 27, chambers 26 being on the side facing the infra-red bulbs 24.

Each chamber 27 connects with a respective compression chamber 28 by way of respective connecting ports 29. A piston 30 is mounted in each compression chamber 28 for reciprocal movement. A piston rod 31 connects each piston 30 respectively to a portion of tie rod 32 on opposite sides of pivot pin 33. Pivot pin 33 is mounted on a pivot post 34 which extends through the base 35 of the block 21. A compression spring 36 biases the pivot post 34 in a direction inwardly of the block 21. The piston rods 31 also extend through the base 35 and are biased in a direction inwardly of the block 21 by compression springs 37. The springs 37 at one end bear against the lower edge of respective connecting portions 38 of tie rod 32 on opposite sides of pivot pin 33, and the other end of springs 37 bears against a bearing ring member 39 which rests against the inner face of the base 35 of the block 21. The outer ends of piston rods 31 are threaded and extend through base 35 to threadedly receive nuts 40 thereon. The tension of springs 37 and relative force required to move pistons 30 can be adjusted and balanced by tightening or loosening the nuts 40. Rotating nuts 40 in a tightening direction will increase the tension on the respective spring 37 and will increase the force required to move the respective piston 30 against the bias of such spring. The tension of springs 37 is adjusted so the same amount of force is required on each piston 30 to move it against the bias of its respective spring 37.

Tie rod 32 includes an extended portion 41 at one end which projects outwardly of the side wall of block 21. The outer end of extended portion 41 is positioned above and in alignment with a switch assembly 42. When the pressure on piston 30b becomes greater than the pressure on piston 30a, the extended portion 41 of tie rod 32 is moved downwardly into engagement with the operating button 43 of switch assembly 42. Such engagement with switch operator 43 energizes control circuit 20 by a signal from the mechanical detector 2.

Mechanical detector 2 operates in the following manner. Chamber 22 has an aperture 45 extending through its side wall and positioned below the infra-red lamp 24a. The aperture 45 is connected to an exhaust blower 46. A second aperture 47 extends through the side wall of chamber 22 near its opposite end, just above its lens 25. This aperture 47 is connected to a flexible tube 48 having a screened intake head or detector head 49 at one end for positioning at a desired place within the compartment or room being monitored. A plurality of detector heads 49 may be connected to respective ones of a plurality of apertures 47 to monitor and detect air samples at a plurality of locations within the compartment or room being monitored for carbon monoxide.

Chamber 23 of the mechanical detector 2 includes an intake aperture 50 and outlet aperture 51, both connected to a reference air tank 52. An intake blower 53 draws fresh air from an outside source through flexible intake tube 54 and feeds such fresh air into chamber 23 through intake aperture 50. The air is exhausted through outlet aperture 51 and a continuous source of reference air uncontaminated by a dangerous level of carbon monoxide is thereby caused to flow continuously through chamber 23.

Both chambers 27 of mechanical detector 2 are filled with equal amounts of carbon monoxide. When the amount of carbon monoxide present in chambers 22 and 23 is equal, the heat generated on the carbon monoxide molecules in both chambers 27 by infra-red lamps 24a and 24b is the same and the pressure in both chambers remains equalized. However, when the passenger compartment of the vehicle being monitored begins to fill up with carbon monoxide, the air drawn into chamber 22 through intake detector head 49 begins to contain a higher concentration of carbon monoxide than does the chamber 23 having the reference air flowing therein. The infra-red rays from lamp 24a in chamber 22 thus "see" and have to heat more carbon monoxide molecules in the combined chambers 22 and 27a which are aligned with lamp 24a, than do the infra-red rays from lamp 24b in chamber 23 which "see" and heat the carbon monoxide molecules in combined chambers 23 and 27b. If the reference air drawn into chamber 23 is completely devoid of carbon monoxide, the only carbon monoxide molecules which are seen and heated by the infra-red rays from lamp 24b are those in chamber 27b.

When the infra-red rays from lamp 24a extending through chambers 22 and 27a see and heat a greater number of carbon monoxide molecules than do those from lamp 24b, both lamps being of the same output capacity, the heat generated on the fewer carbon monoxide molecules in chambers 23 and 27b is proportionately greater and the pressure generated in chamber 27b becomes proportionately higher than the pressure in chamber 27a. Piston 30b is thereby caused to move relative to piston 30a, either a greater distance than piston 30a or in an opposite direction from any movement of piston 30a, causing the pivoted tie rod 32 to in turn pivot on pivot pin 33. When the differential pressure becomes great enough, the extended portion 41 of tie rod 32 will eventually move sufficiently to engage the switch operator 43 of switch assembly 42 and thus energize the control circuit 20 to provide a signal from the mechanical detector 2 that a pre-determined dangerous level of carbon monoxide is present in the monitored compartment or room. The amount of carbon monoxide differential between the reference air source and the monitored air which will cause the extension 41 of tie rod 32 to engage and close the switch assembly 42 may be varied by adjusting the tension of springs 37. The greater the tension of springs 37, the greater amount of differential that will be required for mechanical detector 2 to respond. Or, stated another way, the greater the tension on compression springs 37, the higher the level of concentration of carbon monoxide in the monitored compartment or room that will be required for the mechanical detector 2 to respond.

When the electrical detector 1 and the mechanical detector 2 both send a signal to the control circuit 20 that the pre-determined dangerous level of carbon monoxide is present, control circuit 20 responds by closing a circuit between the vehicle battery 55 and solenoid 56 thus energizing the solenoid with the voltage of the battery, preferably 12 volts. The solenoid when energized opens a vacuum valve 57 which enables the vacuum manifold 58 of internal combustion engine 59 to supply a vacuum to the vacuum operated switch 60 through vacuum tube 61. Control circuit 20 includes two switches which may be electro-mechanical relays, or electronic switches such as a pair of transistors or a pair of SCRs (silicon controlled rectifiers) connected in a well known manner, so that a signal from the electrical detector 1 renders one of such switches conductive and a signal from mechanical detector 2 renders the other of such switches conductive, and so that it is only when both of said switches are conductive than an operative voltage or current is transmitted from the control circuit 20 to other operating components of the system.

The vacuum operated switch 60 is biased to the normally closed position by compression spring 62 bearing against contact plate 63, which electrically connects contact 64 connected to ground with contact 65 which is connected in the ignition circuit with ignition switch 66 to the electrical distribution circuit of the internal combustion engine. When vacuum valve 57 is opened by energization of the solenoid 56 on occurrence of a dangerous level of carbon monoxide concentration sensed by both detectors, a vacuum is supplied by the engine manifold 58 to the vacuum chamber 67 of the vacuum operated switch 60. Such vacuum causes contact plate 63 to separate from contacts 64 and 65 against the bias of spring 62 thus opening the ignition circuit of the internal combution engine 59. The ignition circuit will remain open as long as the engine continues to run and supply a vacuum from its manifold 58 to the vacuum operated switch 60. When the internal combustion engine 59 finally stops, a vacuum will no longer be supplied to vacuum operated switch 60 and contact plate 63 will again be urged to a contact closed position under the bias of spring 62 thus making electrical contact again between contacts 64 and 65. The ignition circuit thereby re-closes automatically by means of the vacuum operated switch 60 after the internal combustion engine has ceased operation. The vacuum operated switch connected to the vacuum manifold of the internal combustion engine being monitored provides a positive method of insuring that the electrical circuit of the engine remains open until the engine is brought to a complete stop. Other types of switches, delay mechanisms and reset devices, such as electrical or electronic timing circuits to open and reset the electrical distribution circuit of the engine, may reclose or reset the electrical circuit of the engine after a delay which is thought to be sufficient but because of "dieseling" or "running on" by self combustion without electrical ignition the engine may still be running. If the circuit is reclosed while the engine is still dieseling it would restart and continue to supply carbon monoxide. The vacuumm operated switch 60 prevents such occurrence and keeps the electrical circuit of the engine open as long as the engine is running by whatever means and supplying a vacuum in its manifold 58.

A separate vacuum storage tank 68 may be provided to open a fresh air vent assembly 69 upon occurrence of a dangerous level of carbon monoxide sensed by both detectors 1 and 2. The solenoid 56 may be connected to also open vacuum or air valve 70 in the vacuum tube 71 leading from vacuum storage tank 68 to fresh air vent 69, whereupon the vacuum in tank 68 provides a vacuum to the vacuum chamber 72 of the fresh air vent assembly 69. Such vacuum is sufficient to overcome the oppositely directed bias of spring 73 against vacuum plate 74, thus causing vacuum plate 74 to draw the vent closure member 75 away from vent opening 76. The fresh air vent assembly 69 is mounted inside of the passenger compartment or other room or compartment being monitored, with the vent closure member 75 mounted in a wall of the compartment with its vent opening 76 in communication with the outside fresh air. When vent closure member 75 is drawn away from vent opening 76 under the influence of the vacuum supplied by vacuum tank 68, fresh air enters the intake chamber 77 and passes through the annular screen 78 which surrounds intake chamber 77 into the passenger compartment. Thus, at the same time that steps are initiated to stop the internal combustion engine source or carbon monoxide, an auxiliary mechanism is actuated to provide a source of fresh air. The vacuum storage tank 68 is provided with its vacuum by the manifold 58 of engine 59 while it is running. A vacuum is retained in the storage tank 68 after the engine 59 has been stopped, so it is thus able to hold the fresh air vent open even after the engine has ceased operation. The vacuum or air valve 70 is preferably of the one way operation type which opens by action of the solenoid 56 but must be reclosed manually. When reclosed manually to shut off the vacuum supply, the closure member 75 will close against the vent opening 76 under the bias of spring 73 against vacuum plate 74.

I claim:

1. A carbon monoxide detector assembly, including means defining a compartment, a first detecting means defining an electrical detector to detect a pre-determined amount of carbon monoxide in said compartment and respond thereto, a second detecting means defining an electro-mechanical detector to detect the same pre-determined amount of carbon monoxide in said same compartment and respond thereto, means defining an internal combustion engine source of carbon monoxide, signal means to signal the presence of a dangerous level of carbon monoxide concentration when detected by said first and second detecting means, a deactivating mechanism to discontinue operation of said internal combustion engine source of carbon monoxide upon receipt of a signal from said signal means that a dangerous level of carbon monoxide concentration is present, said deactivating mechanism being responsive to said signal means to cause operation of said internal combustion engine source of carbon monoxide to be discontinued, said deactivating mechanism including automatic reset positive interruption means to automatically restore conditions for operation of said internal combustion engine after interruption thereof by said signal from said signal means, positive indication means to indicate that said internal combustion engine has stopped operation, wherein said deactivating mechanism will not restore conditions for operation of said internal combustion engine until receipt of a positive indication from said positive indication means that said internal combustion engine has stopped operation.

2. A carbon monoxide detector assembly as set forth in claim 1, wherein said automatic reset positive interruption means includes a vacuum operated switch, said internal combustion engine having an electrical ignition circuit, a vacuum manifold of said internal combustion engine, a vacuum chamber in said vacuum operated switch, said vacuum chamber being provided a vacuum from said vacuum manifold upon receipt of said signal that a dangerous level of carbon monoxide concentration is present, said vacuum operated switch including separable contact means separable on said vacuum chamber being provided with said vacuum from said manifold of said internal combustion engine, said contact means remaining separated as long as a vacuum is provided by said manifold, said contact means being movable back to the contact closed position upon discontinuance of said vacuum from said manifold.

3. A carbon monoxide detector assembly as set forth in claim 2, wherein said vacuum operated switch is in said ignition circuit, said ignition circuit being interrupted on receipt of a vacuum by said vacuum operated switch from said manifold of said internal combustion engine, said ignition circuit being retained in the interrupted state as long as said internal combustion engine continues to operate and supply a vacuum from its manifold to said vacuum operated switch, said vacuum operated switch including bias means to bias said separable contact means toward the contact closed position, said ignition circuit being automatically reclosed when said internal combustion engine stops operating and its manifold discontinues its vacuum supply to said vacuum chamber of said vacuum operated switch.

4. A carbon monoxide detector assembly as set forth in claim 1, including a vacuum storage tank, a vacuum operated fresh air vent assembly mounted in said compartment being monitored and opening to a source of fresh air, valve means connected between said vacuum storage tank and said fresh air vent assembly, and control means to open said valve means on receipt of said signal that a dangerous level of carbon monoxide concentration is present whereupon said vacuum in said vacuum storage tank causes said fresh air vent assembly to open and admit uncontaminated fresh air into said compartment being monitored.

* * * * *